United States Patent [19]

Sandoval

[11] Patent Number: 5,715,583
[45] Date of Patent: Feb. 10, 1998

[54] APPARATUS FOR PRESERVING A CADAVER AND METHOD THEREFOR

[76] Inventor: Juan Sandoval, 2038 S. Plaza, N.W. Albuquerque, N. Mex. 87104

[21] Appl. No.: 778,160

[22] Filed: Jan. 10, 1997

[51] Int. Cl.⁶ ..................................................... A61G 17/00
[52] U.S. Cl. ..................................................... 27/11; 27/23.1
[58] Field of Search ........................... 27/21.1, 22.1, 27/23.1, 2, 11

[56] References Cited

U.S. PATENT DOCUMENTS

| | | | |
|---|---|---|---|
| 2,296,539 | 9/1942 | Salle | 27/22.1 |
| 4,879,789 | 11/1989 | Bak | 27/11 |
| 4,924,565 | 5/1990 | Rathjen | 27/11 |
| 5,216,789 | 6/1993 | Pomares et al. | 27/23.1 |

*Primary Examiner*—Kien T. Nguyen
*Attorney, Agent, or Firm*—Harry M. Weiss; Jeffrey D. Moy; Harry M. Weiss & Associates, P.C.

[57] ABSTRACT

The present invention is directed to an apparatus and method for preserving cadavers. The apparatus is preferably comprised of a container that receives a cadaver, which cadaver has first been placed into a multi-layered plastic bag of the type used in the vacuum-packing industry. The container has the ability to be sealed in a substantially air-tight manner. Located on or coupled to the container is a gas evacuation apparatus, which evacuates substantially all of the gases within the container, the bag, and the cadaver. The cadaver is then sealed using a sealing apparatus located within the cadaver. The cadaver, in the sealed bag, may then be removed.

22 Claims, 2 Drawing Sheets

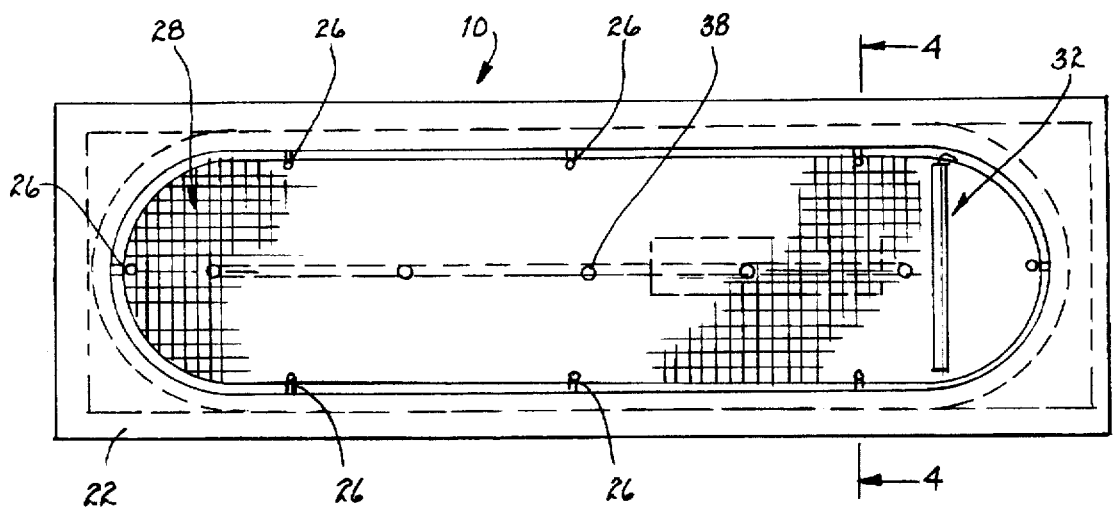
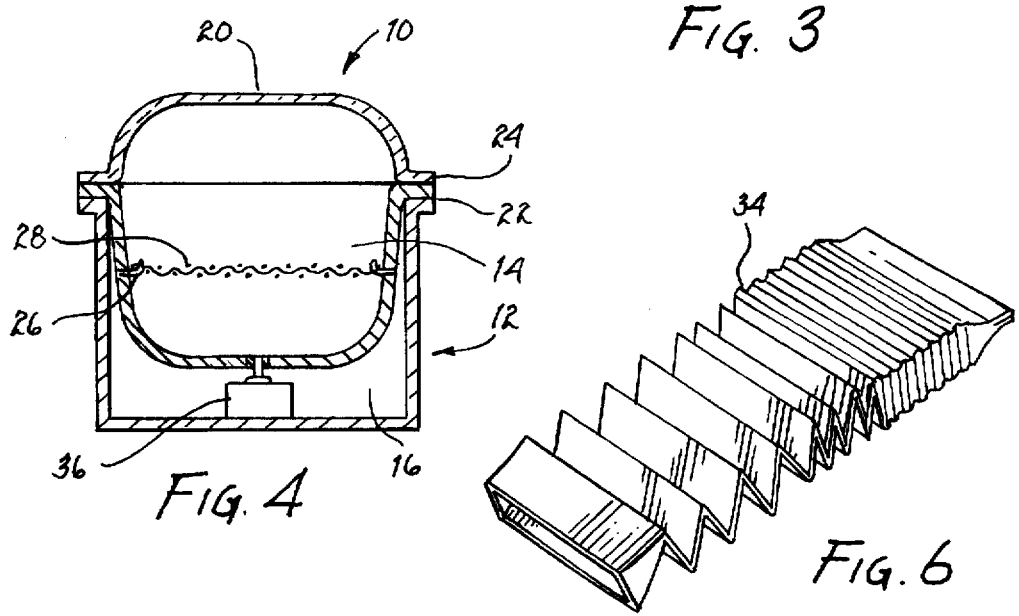
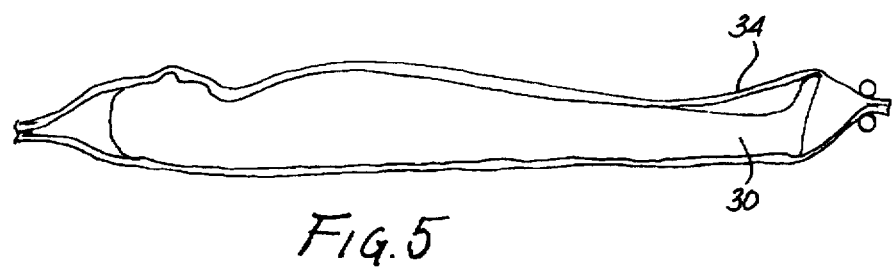

APPARATUS FOR PRESERVING A CADAVER AND METHOD THEREFOR

BACKGROUND OF THE INVENTION

Field of Invention

This invention relates generally to apparatuses and methods for preserving cadavers and, more specifically, to an apparatus and method for preserving a cadaver in a substantially gas-free environment.

BACKGROUND OF THE INVENTION

It is often necessary to preserve human cadavers in a manner that will, to a greater or lesser extent, prevent or at least minimize decomposition. For example, it is often necessary to temporarily preserve a cadaver in a funeral home in anticipation of a wake, burial ceremony and/or cremation. Currently such preservation is generally accomplished through embalming. Cadavers may also be temporarily preserved through the use of refrigeration equipment.

There are a number of drawbacks associated with the existing methods of preserving a cadaver. With respect to embalming, it is an invasive procedure—incisions generally must be made into the body to permit the draining of blood and the insertion of embalming fluids. It requires the use of numerous different chemicals, including preservatives, germicides, modifying agents, anticoagulants, surfactants, dyes, perfuming agents and/or chemical vehicles. Embalming may not be possible with a body that has a communicative disease, and may not be possible or effective with bodies that have been mutilated, damaged, or decomposing. Embalming also cannot readily be accomplished in the field, for example by a coroner, or in some other non-funeral home setting. Furthermore, embalming is unacceptable on religious grounds to certain groups, including Jews, Buddhists, Hindus, Muslims, and Sikhs. For these and other reasons, embalming is largely an American practice, and is not widely used outside of the United States. With respect to refrigeration, it is an expensive method of preservation and one that does not readily lend itself to use with cadavers that are being transported.

Therefore, a need existed to provide an improved apparatus and method for preserving cadavers, which permits the preservation of a cadaver in a non-invasive manner and without the need for embalming or refrigeration. The improved apparatus and method must allow the preservation of cadavers in a manner that will make them readily transportable in a preserved state, that will allow preservation to take place in the field, and that will be acceptable to at least certain of those religious groups that oppose embalming.

SUMMARY OF THE INVENTION

It is an object of the present invention to provide an improved apparatus and method for preserving cadavers.

It is an object of this invention to provide an apparatus and method for preserving cadavers that does not require penetration of the cadaver or the use of preserving fluids.

It is another object of this invention to provide an apparatus and method for preserving cadavers that will make the cadaver readily transportable in a preserved state, without the need for refrigeration.

It is a still further object of this invention to provide an apparatus and method for preserving cadavers that will allow preservation to be accomplished in a field setting, outside of a funeral home or hospital.

It is yet a further object of this invention to provide an apparatus and method for preserving cadavers that will allow preservation to be accomplished in a manner that is acceptable to at least certain of those religious groups that oppose embalming.

BRIEF DESCRIPTION OF THE PREFERRED EMBODIMENTS

In accordance with one embodiment of the present invention, an apparatus for preserving a cadaver is disclosed. The apparatus comprises, in combination: a cadaver; bag means for containing and preserving said cadaver in a substantially gas free environment; container means for receiving said bag means containing said cadaver; means located on said container means for permitting said container means to be sealed in a substantially air-tight manner following the placement therein of said cadaver contained in said bag means; gas extraction means coupled to said container means for evacuating substantially all gases surrounding said cadaver; and means located on said container means for sealing said bag means after the extraction therefrom of the substantially all gases.

In accordance with another embodiment of the present invention, an apparatus for preserving a cadaver is disclosed. The apparatus comprises, in combination: a cadaver; bag means for containing and preserving said cadaver in a substantially gas free environment; and container means for receiving said bag means containing said cadaver; said container means comprising the following: an inner chamber comprising a substantially rectangular shaped container for receiving said bag means containing said cadaver; said inner chamber having an opening through which said bag means containing said cadaver may be placed; support means for supporting said cadaver in a substantially horizontal position within said inner chamber; means located in said inner chamber for permitting said container to be sealed in a substantially air-tight manner following the placement therein of said bag means containing said cadaver; an outer chamber containing gas extraction means for extracting substantially all gases located within each of said cadaver, said bag means, and said inner chamber; and means located in said inner chamber for substantially sealing said bag means after the extraction therefrom of said substantially all gases.

In accordance with a further embodiment of the present invention, a method for preserving a cadaver is disclosed. The method comprises the steps of: providing a cadaver; providing bag means for containing and preserving said cadaver in a substantially gas free environment; inserting said cadaver into said bag means; providing container means for receiving said bag means containing said cadaver; said container means comprising means for substantially sealing said bag means; said container means further comprising means for permitting said container means to be sealed in a substantially air-tight manner following the placement therein of said cadaver contained in said bag means; said container means still further comprising means for sealing said bag means; placing said bag means containing said cadaver into said container means; providing gas extraction means coupled to said container means for evacuating substantially all gases surrounding said cadaver; evacuating substantially all the gases surrounding said cadaver; and substantially sealing said bag means.

In accordance with a further embodiment of the present invention, a further method for preserving a cadaver is disclosed. The method comprises the steps of providing a cadaver; providing bag means for containing and preserving said cadaver in a substantially gas free environment; inserting said cadaver into said bag means; providing container means for receiving said bag means containing said cadaver; said container means comprising means for substantially sealing said bag means; said container means further comprising means for permitting said container means to be sealed in a substantially air-tight manner following the placement therein of said cadaver contained in said bag means; said container means still further comprising means for sealing said bag means; placing said bag means containing said cadaver into said container means; providing gas extraction means coupled to said container means for evacuating substantially all gases surrounding said cadaver; said gas extraction means comprising means for inserting into said container means, said bag means, and said cadaver means a protocol-type gas; inserting into said inner chamber said protocol-type gas; evacuating substantially all the gases surrounding said cadaver; and substantially sealing said bag means.

In accordance with a still further embodiment of the present invention, a method for preserving a cadaver is disclosed. The method comprises the steps of: providing a cadaver; providing bag means for containing and preserving said cadaver in a substantially gas free environment; inserting said cadaver into said bag means; providing container means for receiving said bag means containing said cadaver; said container means comprising the following: an inner chamber comprising a substantially rectangular shaped container for receiving said bag means containing said cadaver; said inner chamber having an opening through which said bag means containing said cadaver may be placed; support means for supporting said cadaver in a substantially horizontal position within said inner chamber; means located in said inner chamber for permitting said inner chamber to be sealed in a substantially air-tight manner following the placement therein of said bag means containing said cadaver; an outer chamber of said container means containing gas extraction means for extracting substantially all gases located within each of said cadaver, said bag means, and said inner chamber; and means located in said inner chamber for substantially sealing said bag means after the extraction therefrom of said substantially all gases; placing said bag means containing said cadaver on said support means; evacuating substantially all the gases surrounding said cadaver; and substantially sealing said bag means.

The foregoing and other objects, features, and advantages of the invention will be apparent from the following, more particular, description of the preferred embodiments of the invention, as illustrated in the accompanying drawings.

BRIEF DESCRIPTION OF THE DRAWINGS

FIG. 3 is a top cross-sectional view of the apparatus for preserving a cadaver of the present invention, taken along line 3—3 of FIG. 2.

FIG. 4 is an end cross-sectional view of the apparatus for preserving a cadaver of the present invention, taken along line 4—4 of FIG. 3.

FIG. 5 is a side view of a cadaver preserved in a bag using the apparatus of the present invention.

FIG. 6 is a perspective view of a bag used for preserving a cadaver in connection with the present invention, folded accordion style for ready use with a cadaver.

DETAILED DESCRIPTION OF THE PREFERRED EMBODIMENTS

Figure 1:
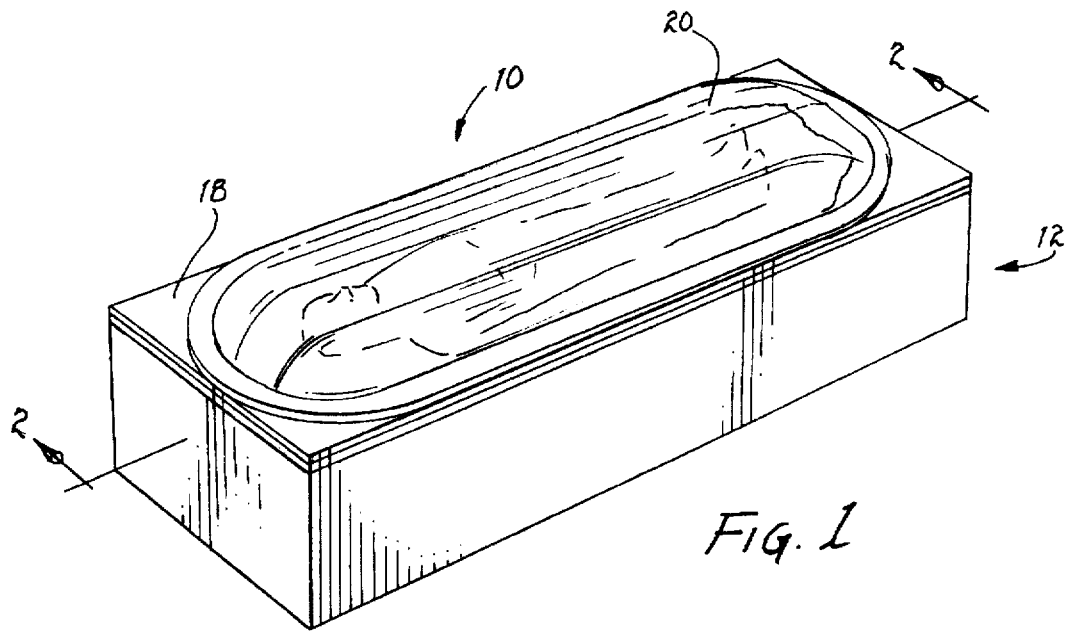
FIG. 1 is a perspective view of one embodiment of the apparatus for preserving a cadaver of the present invention.
Figure 2:
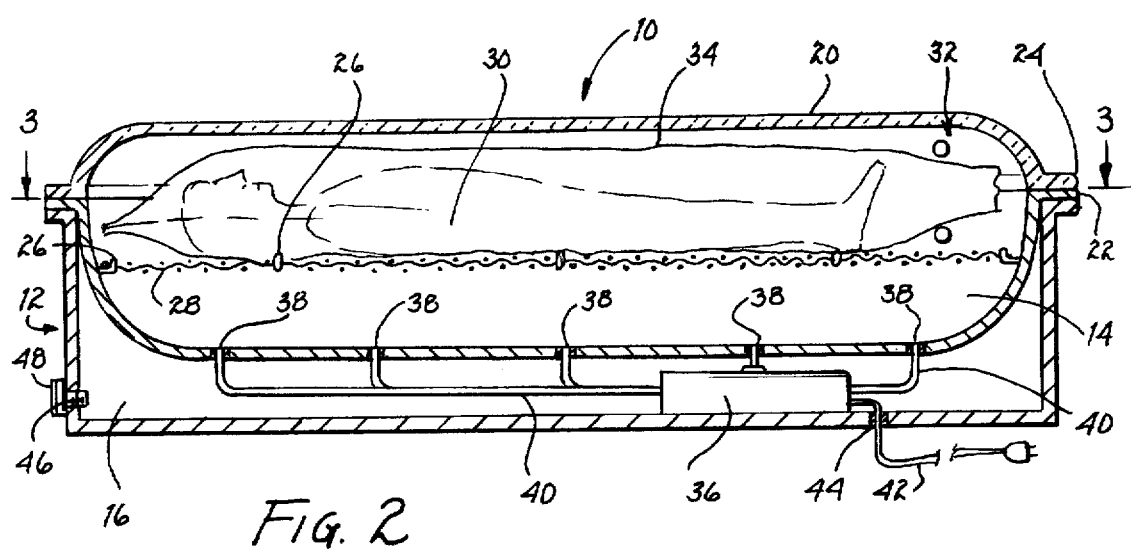
FIG. 2 is a side cross-sectional view of the apparatus for preserving a cadaver of the present invention, taken along line 2—2 of FIG. 1.

Referring to the embodiment of FIGS. 1–4, reference number 10 refers generally to the apparatus for preserving a cadaver of the present invention. The apparatus 10 comprises a substantially coffin-shaped container 12, having an inner chamber 14 and an outer chamber 16. The inner chamber 14 is substantially rectangle shaped, and preferably is gently sloped at each of its two end portions as shown in FIG. 2. The container 12 is covered with a cover 18, which incorporates a substantially bubble-shaped plexiglass top 20, so that a person standing over the apparatus 10 can determine whether or not a cadaver is present in the inner chamber 14 without having to open the cover 18. The container 12, including the inner chamber 14, the outer chamber 16, and the cover 18 (except for the plexiglass top 20) should preferably be manufactured from brushed aluminum or steel to allow easy cleaning. However, other materials may also be used.

Referring now to FIGS. 2 and 3, a lip 22 comprised of rubber grommet or other similar type material is located around a perimeter of a top portion of the inner chamber 14. A corresponding lip 24 is located around a perimeter of the cover 18, so that when the cover 18 is closed, the lips 22 and 24 contact each other to form a substantially air-tight seal.

Referring to FIGS. 2, 3, and 4, located within the inner chamber 14 is a plurality of hooks 26. Preferably, there are three hooks 26 that are welded or otherwise fastened on each of the two long sides of the inner chamber 14 and one hook 26 that is welded or otherwise fastened on each of the short sides of the inner chamber 14, though the number and placement of the hooks may be varied without departing from the spirit or scope of the invention. The hooks 26 should be located at the same height, and support a steel mesh-type tray 28. The hooks 26 should be located at a height within the inner chamber 14 so that the placement of a cadaver 30 onto the tray 28 will not cause the tray 28 to contact the bottom of the inner chamber 14, yet low enough so that the cover 18 may be fully closed with a cadaver 30 present in the inner chamber 14 on the tray 28.

Referring to FIGS. 2 and 3, the inner chamber 14 further comprises a sealing apparatus 32 of the type typically used in the vacuum-packing industry, which generally comprises a pair of opposing parallel bars (as best shown in FIG. 3 and as also shown in FIG. 5) between which an unsealed end of a vacuum-type bag 34 may be placed. When the bag 34 is ready to be sealed, the parallel bars comprising the sealing apparatus 32 are brought together and heated, melting together the previously open end of the bag 34 to form a substantially air-tight seal.

Referring now to FIGS. 2, 3, and 4, a gas extraction apparatus 36 is located within the outer chamber 16 of the container 12. The gas extraction apparatus 36 is of the type currently used in the vacuum-packing industry to extract gases. The gas extraction apparatus 36 may include structure that will permit it to pump into the inner chamber 14 and bag 34 protocol gases such as nitrogen, argon, or a nitrogen/oxygen compound. Located within a base portion of the inner chamber 14 are a plurality of openings 38, into each of which is inserted a hose 40, each of which hoses 40 has its other end in the gas extraction apparatus 36. A power cord 42, which passes through an opening 44 in the base of the container 12, connects the gas extraction apparatus 36 to an external power source (not shown). Alternatively, a power source could be located within the outer chamber 16 or otherwise coupled to the container 12. It would also be possible to locate the gas extraction apparatus 36 outside of the container 12 without departing from the spirit or scope of the invention. An opening 46, which may be closed with a stopper type seal 48, acts as a vent through which gases evacuated from the inner chamber 14 with the gas extraction apparatus 36 may be released outside of the container 12. Where there is a fear of disease or some other contamination from the release of evacuated gases, it is possible to connect a tank or other receptacle (not shown) to opening 46, to receive the evacuated gases in a secure manner for disposal and to prevent them from escaping into the environment.

Referring to FIGS. 5 and 6, the bag 34 is shown. In FIG. 6, the bag 34 is shown prior to the placement therein of a cadaver 30. Preferably, the bag 34, which is open on one of its two short ends, is pleated accordion style as shown in FIG. 6, so that one person may place a cadaver therein by, for example, placing the open end of the bag 34 at the feet of the cadaver 30 and by simply pulling the open end up the cadaver 30 until it passes over the head of the cadaver 30. As the open end of the bag 34 is pulled toward the head of the cadaver 30, the pleats will cause the bag 34 to unfold and increase in size in an orderly fashion. Preferably, bag 34 is comprised of six layers of plastic, and is of a type commonly used in the vacuum-packing industry.

OPERATION OF THE INVENTION

A person wishing to preserve a cadaver 30 using the apparatus 10 of the present invention must first place the bag 34 over the cadaver 30. This can best be accomplished by placing the open end of the bag 34, which bag 34 should be pleated as shown in FIG. 6, over one end of the cadaver 30. The open end of the bag 34 should then be pulled toward the opposite end of the cadaver 30, until the open end has passed over the opposite end of the cadaver 30.

Next, the bag 34, containing the cadaver 30, should be placed onto the tray 28 in the inner chamber 14 of the container 12 so that the open end of the bag 34 is placed at the same end of the inner chamber 14 as the sealing apparatus 32. The open end of the bag 34 should then be passed between the parallel bars comprising the sealing apparatus 32, for later sealing.

Once the bag 34 is in position, the cover 18 should be closed, so that the lips 22 and 24 contact each other to form a substantially air-tight seal. The next step is to evacuate substantially all of the gases located in the inner chamber 14, the bag 34, and the cadaver 30 with the gas extraction apparatus 36. The gas extraction apparatus 36 will evacuate substantially all of these gases through the openings 38 and the hoses 40, which gases may then be expelled though the opening 46. It may also be desired to use during the gas evacuation step protocol gases such as nitrogen, argon or a nitrogen/oxygen compound. When these are used, the protocol gas is pumped into the inner chamber 14 and the bag 34 through the hoses 40 and openings 38. The protocol gases, which are heavier than substantially all of the atmospheric gases present in the body, will force out of the body substantially all of those atmospheric gases. The gas extraction apparatus 36 then evacuates substantially all of the atmospheric and protocol gases, creating a micro-vacuum. This step causes the bag 34 to substantially conform to the shape of the cadaver 30, as shown in FIG. 5.

Once the gas evacuation step has been completed, the open end of the bag 34 may be sealed using the sealing apparatus 32. In this regard, the parallel bars comprising the sealing apparatus 32 are brought toward each other, compressing the open end of the bag 34 between them. The parallel bars are then heated, melting the portion of the bag 34 trapped between them and forming a seal. The parallel bars are then moved apart, and the cover 18 may be opened to permit removal of the bag 34 if desired. The bag 34 may then be placed into another container, perhaps made of cardboard or plastic, or perhaps a vinyl body bag, for transport.

If the cadaver 30 is to be viewed, at a wake for example, or is to be subjected to an autopsy or perhaps dissection for research purposes, it may be preserved additional times using the apparatus 10 of the present invention.

While the invention has been particularly shown and described with reference to preferred embodiments thereof, it will be understood by those skilled in the art that the foregoing and other changes in form and details may be made therein without departing from the spirit and scope of the invention.

I claim:

1. An apparatus for preserving a cadaver comprising, in combination:

a cadaver;

bag means for containing and preserving said cadaver in a substantially gas free environment;

container means for receiving said bag means containing said cadaver;

means located on said container means for permitting said container means to be sealed in a substantially air-tight manner following the placement therein of said cadaver contained in said bag means;

gas extraction means coupled to said container means for evacuating substantially all gases surrounding said cadaver; and means located on said container means for sealing said bag means after the extraction therefrom of the substantially all gases.

2. An apparatus for preserving a cadaver in accordance with claim 1 wherein said bag means is substantially rectangle-shaped and comprises a series of substantially evenly-spaced parallel pleats.

3. An apparatus for preserving a cadaver in accordance with claim 1 wherein said container means comprises the following:

a substantially rectangular shaped container for receiving said cadaver contained in said bag means; and said container having an opening through which said bag means containing said cadaver may be placed into said container.

4. An apparatus for preserving a cadaver in accordance with claim 3 wherein said container means further comprises:

support means for supporting said cadaver in a substantially horizontal position above a base portion of said container means.

5. An apparatus for preserving a cadaver in accordance with claim 4 wherein said support means comprises a rigid mesh-type member having a length greater than a length of said cadaver and a width greater than a width of said cadaver.

6. An apparatus for preserving a cadaver in accordance with claim 1 wherein said gas extraction means are located within said container means.

7. An apparatus for preserving a cadaver in accordance with claim 1 wherein said gas extraction means further comprises means for inserting into said container means, said bag means, and said cadaver means a protocol-type gas.

8. An apparatus for preserving a cadaver in accordance with claim 7 wherein said protocol-type gas comprises one of a group including nitrogen, argon, and a nitrogen/oxygen compound.

9. An apparatus for preserving a cadaver comprising, in combination:

a cadaver;

bag means for containing and preserving said cadaver in a substantially gas free environment; and container means for receiving said bag means containing said cadaver;

said container means comprising the following:

an inner chamber comprising a substantially rectangular shaped container for receiving said bag means containing said cadaver;

said inner chamber having an opening through which said bag means containing said cadaver may be placed;

support means for supporting said cadaver in a substantially horizontal position within said inner chamber;

means located in said inner chamber for permitting said container to be sealed in a substantially air-tight manner following the placement therein of said bag means containing said cadaver;

an outer chamber containing gas extraction means for extracting substantially all gases located within each of said cadaver, said bag means, and said inner chamber; and means located in said inner chamber for substantially sealing said bag means after the extraction therefrom of said substantially all gases.

10. An apparatus for preserving a cadaver in accordance with claim 9 wherein said gas extraction means further comprises means for inserting into said container means, said bag means, and said cadaver means a protocol-type gas.

11. An apparatus for preserving a cadaver in accordance with claim 10 wherein said protocol-type gas comprises one of a group including nitrogen, argon, and a nitrogen/oxygen compound.

12. A method for preserving a cadaver comprising the steps of:

providing a cadaver;

providing bag means for containing and preserving said cadaver in a substantially gas free environment;

inserting said cadaver into said bag means;

providing container means for receiving said bag means containing said cadaver;

said container means comprising means for substantially sealing said bag means;

said container means further comprising means for permitting said container means to be sealed in a substantially air-tight manner following the placement therein of said cadaver contained in said bag means;

said container means still further comprising means for sealing said bag means;

placing said bag means containing said cadaver into said container means;

providing gas extraction means coupled to said container means for evacuating substantially all gases surrounding said cadaver;

evacuating substantially all the gases surrounding said cadaver; and substantially sealing said bag means.

13. The method of claim 12 wherein said bag means comprises a plurality of layers of plastic material.

14. The method of claim 13 wherein said bag means comprises at least six layers of plastic material.

15. The method of claim 12 wherein said bag means is substantially rectangle-shaped and comprises a series of substantially evenly-spaced parallel pleats.

16. The method of claim 12 wherein said container means comprises the following:

a substantially rectangular shaped container for receiving said cadaver contained in said bag means; and said container having an opening through which said bag means containing said cadaver may be placed into said container.

17. The method of claim 16 wherein said container means further comprises:

support means for supporting said cadaver in a substantially horizontal position above a base portion of said container means.

18. The method of claim 17 wherein said support means comprises a rigid mesh-type member having a length greater than a length of said cadaver and a width greater than a width of said cadaver.

19. The method of claim 12 wherein said gas extraction means are located within said container means.

20. A method for preserving a cadaver comprising the steps of:

providing a cadaver;

providing bag means for containing and preserving said cadaver in a substantially gas free environment;

inserting said cadaver into said bag means;

providing container means for receiving said bag means containing said cadaver;

said container means comprising means for substantially sealing said bag means;

said container means further comprising means for permitting said container means to be sealed in a substantially air-tight manner following the placement therein of said cadaver contained in said bag means;

said container means still further comprising means for sealing said bag means;

placing said bag means containing said cadaver into said container means;

providing gas extraction means coupled to said container means for evacuating substantially all gases surrounding said cadaver;

said gas extraction means comprising means for inserting into said container means, said bag means, and said cadaver means a protocol-type gas;

inserting into said inner chamber said protocol-type gas;

evacuating substantially all the gases surrounding said cadaver; and substantially sealing said bag means.

21. The method of claim 20 wherein said protocol-type gas comprises one of a group including nitrogen, argon, and a nitrogen/oxygen compound.

22. A method for preserving a cadaver comprising the steps of:

providing a cadaver;

providing bag means for containing and preserving said cadaver in a substantially gas free environment;

inserting said cadaver into said bag means;

providing container means for receiving said bag means containing said cadaver;

said container means comprising the following:
- an inner chamber comprising a substantially rectangular shaped container for receiving said bag means containing said cadaver;
- said inner chamber having an opening through which said bag means containing said cadaver may be placed;
- support means for supporting said cadaver in a substantially horizontal position within said inner chamber;
- means located in said inner chamber for permitting said inner chamber to be sealed in a substantially air-tight manner following the placement therein of said bag means containing said cadaver;
- an outer chamber of said container means containing gas extraction means for extracting substantially all gases located within each of said cadaver, said bag means, and said inner chamber; and
- means located in said inner chamber for substantially sealing said bag means after the extraction therefrom of said substantially all gases;

placing said bag means containing said cadaver on said support means;

evacuating substantially all the gases surrounding said cadaver; and substantially sealing said bag means.

* * * * *